(12) United States Patent
Zhou et al.

(10) Patent No.: US 8,586,549 B2
(45) Date of Patent: Nov. 19, 2013

(54) COMPOSITION AND METHOD FOR MODULATING AND MAINTAINING VAGINAL BACTERIAL FLORA AND VAGINAL ACIDITY

(75) Inventors: Ruyun Zhou, Guangdon (CN); Zhongming Zeng, Guangdong (CN)

(73) Assignees: Shenzhen Phlora Biotechnology Limited, Shenzhen (CN); HK Phlora Health Sci & Tech. Limited, Hong Kong (CN)

(*) Notice: Subject to any disclaimer, the term of this patent is extended or adjusted under 35 U.S.C. 154(b) by 0 days.

(21) Appl. No.: 13/538,283

(22) Filed: Jun. 29, 2012

(65) Prior Publication Data

US 2012/0263667 A1    Oct. 18, 2012

Related U.S. Application Data

(63) Continuation of application No. 11/912,851, filed as application No. PCT/CN2006/000826 on Apr. 27, 2006, now abandoned.

(30) Foreign Application Priority Data

Apr. 27, 2005    (CN) .......................... 2005 1 0070307

(51) Int. Cl.
  *A61K 31/70*        (2006.01)
(52) U.S. Cl.
  USPC .......................................................... 514/23
(58) Field of Classification Search
  None
  See application file for complete search history.

(56) References Cited

U.S. PATENT DOCUMENTS

| | | | |
|---|---|---|---|
| 6,440,949 B1 | 8/2002 | Zeng | |
| 6,632,796 B1 | 10/2003 | Zeng | |
| 6,849,256 B1 | 2/2005 | Farmer | |
| 2004/0009223 A1 | 1/2004 | Garg et al. | |
| 2004/0110721 A1 | 6/2004 | Zeng | |
| 2004/0192598 A1 | 9/2004 | Kragie | |
| 2005/0080038 A1 | 4/2005 | Bentley et al. | |
| 2006/0105963 A1 | 5/2006 | Yang et al. | |

FOREIGN PATENT DOCUMENTS

| | | |
|---|---|---|
| EP | 0 257 007 A1 | 2/1988 |
| EP | 1 072 268 A1 | 1/2001 |
| EP | 1 072 269 A1 | 1/2001 |
| WO | 95/00133 A1 | 1/1995 |
| WO | 97/29763 A1 | 8/1997 |
| WO | 99/26635 A1 | 6/1999 |
| WO | 99/26636 A1 | 6/1999 |
| WO | 03/079981 A2 | 10/2003 |

OTHER PUBLICATIONS

USPTO NFOA mailed Aug. 19, 2011 in connection with U.S. Appl. No. 11/912,851.
USPTO FOA mailed Jan. 30, 2012 in connection with U.S. Appl. No. 11/912,851.
Supplemental European Search Report dated Jun. 18, 2009; EP 06 74 1747.
International Search Report: mailed Aug. 10, 2006; PCT/CN2006/000826.
Japanese Office Action mailed Mar. 12, 2012; Patent Application No. 2008-508058.

*Primary Examiner* — Allison Ford
*Assistant Examiner* — Yvonne Pyla
(74) *Attorney, Agent, or Firm* — Ladas & Parry LLP

(57) ABSTRACT

The present invention relates to the use of benzoic acid and/or its sodium salt in combination with saccharide(s) as active components in the manufacture of a vaginal composition for modulating vaginal flora and vaginal acidity, thereby maintaining the pH value of vaginal secretion within a range from 3.5 to 4.5; and the present invention further relates to a vaginal composition and a method for modulating and maintaining normal vaginal flora and vaginal acidity.

12 Claims, No Drawings

COMPOSITION AND METHOD FOR MODULATING AND MAINTAINING VAGINAL BACTERIAL FLORA AND VAGINAL ACIDITY

TECHNICAL FIELD

The present invention relates to the use of benzoic acid and/or its sodium salt in combination with saccharide(s) as active components for preparing a vaginal composition for modulating vaginal bacterial flora and vaginal acidity, thereby maintaining the pH value of vaginal secretion within the range from 3.5 to 4.5; the present invention further relates to a vaginal composition, which can be a cleaning—nursing product, a deodorizing agent, a cosmetic, a disinfectant composition, or a pharmaceutical composition; and the present invention further relates to a method for modulating vaginal bacterial flora and vaginal acidity, thereby maintaining the pH value of vaginal secretion within the range from 3.5 to 4.5.

BACKGROUND ART

The surface of female vaginal mucous is suitable for microorganisms such as bacteria, fungi, etc. to inhabit. The dominant bacteria inhabited on healthy vaginal mucous surface are large Gram-positive rods, usually called "vaginal normal flora". Most of these large Gram-positive rods belong to lactobacilli. They are capable of producing acids by metabolizing substances such as glycogen in vaginal mucous epithelial cells so as to maintain the vaginal acidity within a pH value range from 3.5 to 4.5, inhibit pathogens, and resist infection. Undoubtedly, they play a very important role in the health of female genital tract. The abnormal changes of the vaginal flora and acidity usually cause a series of disorders including genital tract infections.

Many factors may disturb vaginal flora and vaginal acidity. Thereby, the large Gram-positive rods would be reduced while a variety of Gram-negative rods and cocci increase and dominate. The pH value of vaginal secretion would be elevated to 4.8, even 5.4 or higher. Complaints such as vulvodynia, pruritus vulvae, algopareunia, abnormal leucorrhea with fishy smell, etc. would be common in these individuals. The vaginal resistance of the patient against infections usually decreases so as to increase the risk to STD and HIV infections. The abnormal changes of vaginal flora may also induce infections in urinary system, and is especially harmful to the health of pregnant women and fetus, including serious consequences such as abortion, premature delivery, intrauterine growth retardation of fetus, etc.

Among various vaginal infections, Candidal vaginitis, Bacterial vaginosis (BV), Lactobacillosis (LB) and Cytolytic vaginosis (CV) are four common diseases. However, their pathogenesises are all related to the abnormality of vaginal flora and vaginal acidity.

Candidal vaginitis is commonly deemed as an endogenous infection. It usually relates to the overgrowth of monilia and the toxin produced thereby in acidic microenvironment, which is formed by acids produced by lactobacilli in vagina. The monilial hypha or spore could be found in the patient's vaginal secretion. The pH value of vaginal secretion usually is lower than 4.5. The clinical symptoms include pruritus vulvae, vulvar causalgia, odynuria, algopareunia, etc. The symptoms are usually most serious before menstruation and alleviated during and after menstruation. Therapeutic methods include the administration of various antifungal agents or antibiotics, such as ketoconazole, nystatin, etc.

Lactobacillosis and Cytolytic vaginosis similarly relate to the over-production of acids by vaginal lactobacilli. Large and long Gram-positive rods are observable in vaginal secretion, while monilial hypha or spore could not be found. Usually, the vaginal acidity of patient is over-high, and the pH value of vaginal secretion is below 4.0 in general. The clinical symptoms are similar with those of Candidal vaginitis, including pruritus vulvae, vulvar causalgia, odynuria, algopareunia, etc., which usually are most serious before menstruation and are obviously alleviated during and after menstruation, as periodic episode. Therapeutic methods mainly include the bidet cleaning with alkali solution of sodium bicarbonate to neutralize the high acidity of vaginal secretion, and the administration of antibiotic Augmentin (Amoxicillin+Clavulanic acid) to inhibit lactobacilli.

Bacterial vaginosis is also an endogenous infection, but its pathogenesis is different from those of the aforementioned diseases. The main reasons are the reduction of vaginal lactobacilli and the reduction of vaginal acidity, which result in the overgrowth of many microorganisms including anaerobic bacteria, etc. and cause various disorders, so that Bacterial vaginosis is also called as "polymicrobial syndrome". The pH value of vaginal secretion usually is higher than 4.5, and the clinical symptoms include pruritus, homogeneous and fishy smell leucorrhea, etc., which are serious after menstruation and are alleviated before menstruation. Internationally, the medicine for treatment of this disease is primarily selected from antibacterial agents such as metronidazole, clindamycin, etc., which exhibit strong effect on anaerobic bacteria.

In sum, although Candidal vaginitis, Lactobacillosis, Cytolytic vaginosis, and Bacterial vaginosis are different diseases in aspects of etiology, pathology, diagnosis and treatment, they all relate to vaginal flora and vaginal acidity: either as Lactobacillosis, Cytolytic vaginosis and Candidal vaginitis caused by the over-production of acids by lactobacilli, or as Bacterial vaginosis caused by the reduction of vaginal lactobacilli and the reduction of vaginal acidity. It can be seen that the abnormality of vaginal flora and vaginal acidity plays a very important roles in the occurrence and development of these vaginal diseases.

However, the current methods for treatment of these diseases mainly aim at the pathogens that cause the diseases. For example, the treatment of Candidal vaginitis is conducted by inhibiting and/or killing fungi with antifungal agents selected from fluconazol, nystatin, etc. The treatment of Bacterial vaginosis is conducted by directly killing anaerobic bacteria with antibacterial agents selected from metronidazole, etc. The treatment of Lactobacillosis and Cytolytic vaginosis is conducted by inhibiting lactobacilli with antibacterial agents selected from Augmentin, etc. The essential problem of how to modulate and maintain vaginal flora and vaginal acidity to normal status, however, is not considered in the art. The treatment methods and medicines for killing pathogens have a lot of drawbacks, such as aggravating the abnormality of vaginal flora and vaginal acidity, therefore, make the conditions be complex, recurrent, and so on.

In Chinese invention patents ZL98809508.4 and ZL98809507.6, and U.S. Pat. No. 6,632,796 and U.S. Pat. No. 6,440,949, the inventors of the present invention had disclosed a composition comprising saccharides as effective component for promoting the growth of vaginal Gram-positive rods and increasing vaginal acidity and uses thereof. The problem of how to promote the growth of vagina lactobacilli was well solved by the compositions and uses in these inventions. The vaginal acidity can be effectively elevated and the pH value of vaginal secretion can be decreased. Thus the reduction of large Gram-positive bacilli and the acidity in vagina, the bacterial vaginosis, and vaginal dysbacteriosis could be treated. However, Lactobacillosis and Cytolytic vaginosis as well as Candidal vaginitis, which are related to the over-production of acids by vaginal lactobacilli and the excessive vaginal acidity, cannot be treated.

SUMMARY OF THE INVENTION

The object of the present invention is to provide a composition for modulating vaginal flora and vaginal acidity in order to maintain the pH value of vaginal secretion within the range from 3.5 to 4.5, and a use of the composition for cleaning-nursing vagina, improving leucorrhea property, eliminating or alleviating the fishy smell of leucorrhea, and eliminating or alleviating complaints such as pruritus vulvae, vulvar causalgia and so on, thereby treating Lactobacillosis, Cytolytic vaginosis, Candidal vaginitis, Bacterial vaginosis, vaginal dysbacteriosis, or other vaginal diseases.

For seeking a composition capable of modulating and maintaining normal vaginal flora and vaginal acidity, the inventors conducted deep and wide researches. The study and experiments on products, medicines and therapeutic methods in the prior art indicate that there is not a product and method that can inhibit the over-production of acids by lactobacilli and can also promote lactobacilli when they are reduced in amount. There is not a product and method that can reduce vaginal acidity when it is excessively strong and can also increase vaginal acidity when it is reduced and weak, thereby continuously maintaining the vaginal pH value within the range from 3.5 to 4.5. After experiments and deep studying, the inventors of the present invention surprisingly found that benzoic acid and/or its sodium salt exhibited relatively strong inhibition effect on the growth and acid-production of lactobacilli under a relatively low pH value (e.g., pH<4.0), and the lower the pH value, the stronger the inhibition effect. However, the inhibition effect on the growth and acid-production of lactobacilli became weak under a relatively high pH value (e.g., pH>4.6), and the higher the pH value, the weaker the inhibition effect.

In particularly, the inventors of the present invention surprisingly found that a novel composition comprising benzoic acid and/or its sodium salt in combination with saccharide(s) was able to modulate vaginal flora and vaginal acidity. When vagina contained less lactobacilli and more Gram-negative rods and cocci and vaginal secretion had a pH value higher than its normal range, benzoic acid and/or its sodium salt exhibited weak inhibition effect on lactobacilli so that lactobacilli grew and produced acids under the stimulation of saccharide and decreased the pH value of vaginal secretion; while when lactobacilli over produced acids and vaginal secretion had a pH value lower than its normal range, benzoic acid and/or its sodium salt exhibited strong inhibition effect on lactobacilli so that lactobacilli produced less acids and the pH value of vaginal secretion increased. Thus, whatever was the original vaginal flora and vaginal acidity, the composition of the present invention could maintain lactobacilli as the dominant bacteria in vagina and maintain the pH value of vaginal secretion within the range from 3.5 to 4.5.

The composition and method of the present invention solve the essential problem of how to modulate and maintain normal vaginal flora and vaginal acidity, exhibit effects of cleaning-nursing vagina, improving leucorrhea property, eliminating or alleviating fishy smell of leucorrhea, eliminating or alleviating symptoms such as vulvodynia, algopareunia, pruritus vulvae, etc., thus can be used for the treatment of not only Lactobacillosis, Cytolytic vaginosis and Candidal vaginitis, but also Bacterial vaginosis and vaginal dysbacteriosis. It is totally different from therapeutic theories, therapeutic models and therapeutic methods in the prior art, i.e., the present invention provides a novel approach for treatment of infectious diseases in vagina. The present invention has been accomplished by the inventor based on the above discovery and further studies.

The present invention provides the use of benzoic acid and/or its sodium salt in combination with saccharide(s) as active components for preparing a vaginal composition for modulating vaginal bacterial flora and vaginal acidity, thereby maintaining the pH value of vaginal secretion within the range from 3.5 to 4.5.

According to the manufacture use of the present invention, the said saccharide(s) is glucose, fructose, mannose, or oligosaccharides or polysaccharides that can be hydrolyzed in vivo or vitro to produce glucose, fructose and/or mannose, or any mixtures of these saccharides, wherein the said oligosaccharides or polysaccharides include but are not limited to the following: sucrose, maltose, lactose, lactulose, trehalose, cellobiose, melibiose, raffinose, malto-oligosaccharide, isomalto-oligosaccharide, fructo-oligosaccharide, dextrin, starch and glycogen; preferably the said saccharide is glucose, fructose, mannose, sucrose, maltose, trehalose, cellobiose, melibiose, malto-oligosaccharide, fructo-oligosaccharide, dextrin, starch or a mixture thereof; more preferably the said saccharide is glucose, fructose, sucrose, maltose or a mixture thereof.

Glucose, fructose and mannose are similar in molecular structure. Under catalysis of dilute base, glucose can be converted into fructose and mannose by enolization, mannose can be converted into glucose and fructose, and fructose can be converted into glucose and mannose. Lactobacilli in vagina ferment monosaccharide such as glucose and fructose to produce acids, such as lactic acid through homo fermentation or hetero fermentation, or acetic acid and lactic acid through Bifidum pathway. Oligosaccharide, starch, glycogen and other macromolecular polysaccharide can be hydrolyzed to produce glucose, fructose and other monosaccharides, and further fermented to produce acids. When vaginal acidity is weak, lactobacilli grow and produce acids under the stimulation of saccharides to maintain normal acidic environment in vagina, to inhibit the growth of Gram-negative bacteria. Lactobacilli dominate. Therefore, both the vaginal flora and vaginal acidity restore normal. However, if vaginal acidity continuously increases, lactobacilli will be inhibited by benzoic acid and/or its sodium salt and produce less acids. Thus, under the alternative action of saccharides and benzoic acid and/or its sodium, the vaginal acidity is maintained within the range from 3.5 to 4.5.

According to the manufacture use of the present invention, benzoic acid solely, or its sodium salt (i.e., sodium benzoate) solely, or a mixture of benzoic acid and sodium benzoate in any proportion could be used. If benzoic acid is used, the amount of benzoic acid is converted into the amount of sodium benzoate according to the proportion that 1.0 g of benzoic acid is equivalent to 1.18 g of sodium benzoate, and then the total amount of sodium benzoate in composition is calculated thereby.

The manufacture use of the present invention is useful for preparing many dosage forms of vaginal composition such as cleaning-nursing products, deodorizing agents, cosmetics, disinfectants and medicines (non-prescription drugs or prescription drugs), including but not limited to the following: water soluble gels, solutions, aerosols, creams, ointments, capsules, microcapsules, suppositories, tablets, preferably water soluble gels, capsules, tablets. The manufacture process technology, method and adjuvants are available by those ordinary skilled in the art according to the disclosures of the present invention in combination with background knowledge in the art.

For example, the water soluble gel composition can be prepared according to the following process flow based on methods known by those skilled in the art: mixing benzoic acid and/or its sodium salt, saccharide and water soluble viscous gel matrix (such as Xanthan gum) in a prescribed proportion, adding a prescribed amount of distilled water, stirring to dissolve sodium benzoate and saccharide and to swell the water-soluble viscous gel matrix to form a homogenous viscous gel, wherein if benzoic acid instead of sodium benzoate is used, it should be dissolved with an amount of ethanol and then added into the gel composition; modulating the pH value of the composition to a range from 3.5 to 7.5, preferably 4.5 to 6.5, by using a pharmaceutical acceptable acid and/or base; sterilizing by a process selected from: radiation sterilization, or high-temperature sterilization at 110-115° C. for 15-20 minutes, or batch sterilization (for example, firstly treating at 70-80° C. for 30 min, then at 36° C. for 5-10 hours, 70-80° C. for 30 min, 36° C. for 5-10 hours again, and finally at 70-90° C. for 30 min), or filtering and sterilizing separately the solution of benzoic acid and/or its sodium salt and the solution of saccharide and then adding them into a sterilized water-soluble gel matrix.

Vaginal tablets can be manufactured based on the methods known by those skilled in the art by mixing benzoic acid and/or its sodium salt with saccharide and then directly tableting to obtain tablets, wherein adjuvants such as magnesium stearate as lubricant or sodium carboxymethyl starch as disintegrant can also be added, mixed and tableted.

Vaginal suppositories can be manufactured according to the following process flow based on methods known by those skilled in the art: mixing and grinding benzoic acid and/or its sodium salt, saccharide and Tween 80, heating to about 50° C., heating separately a mix fatty glyceride (also called: Solid Fat) to 60° C. until melting, then adding the mixture liquid of benzoic acid and/or its sodium salt, saccharide and Tween 80 into the melting matrix under stirring, mixing homogeneously, pouring into a mould at about 40° C. (i.e., before coagulation), little cooling and scraping the mould, cooling and demolding to obtain the vaginal suppositories. Besides mix fatty glyceride, propylene glycol stearate, glycerogelatin, Tween 61, etc. can also be used as the matrix of the said suppositories. Automatic and mechanical devices can be used in large scale production.

According to the manufacture use of the present invention, the total amount of saccharide in the water soluble gel composition is 0.1-20.0% (w/v), preferably 0.5-12.0% (w/v); and the total amount of benzoic acid (calculated based on sodium benzoate) and/or its sodium salt is 0.01-5.0% (w/v), preferably 0.1-1.0% (w/v), more preferably 0.2-0.5% (w/v).

According to the manufacture use of the present invention, the water soluble gel composition further uses a non-flowable, viscous, water-soluble gel matrix, which enables benzoic acid and/or sodium salt and saccharide to homogenously contact with vaginal mucosa and to stay there for a relatively long time, thereby facilitating the modulation of bacterial flora and acidity. The said water-soluble viscous gel matrix is selected and used according to the knowledge of those skilled in the art. According to the manufacture use of the present invention, the matrix includes but is not limited to Xanthan gum, polycarbophil.

The pH value of water-soluble gel composition as prepared according to the present invention is modulated within the range from 3.5 to 7.5, preferably 4.5 to 6.5. The kind and concentration of the acid or base for modulating the pH value of the said composition are knowledge of those ordinary skilled in the art.

The water-soluble gel composition comprising benzoic acid and/or its sodium salt, saccharide as manufactured according to the present invention is packaged in a sealing and sterilizing manner, preferably a single dose packaged in a sealing and sterilizing manner. The sterilization process well known by those skilled in the art can be used for sub-packaging and sealing the sterilized or sterilization-treated composition, or for sub-packaging and sealing the prepared composition and then sterilizing, or sub-packaging the prepared composition in a disposable device for intra-vaginal administration, sealing with overwrap, sterilizing by radiation, etc.

According to the manufacture use of the present invention, one or more antibacterial agents and/or bactericides effective to bacteria and/or fungi are optionally used. The use of antibacterial agents and/or bactericides with strong action on fungi, Gram-negative anaerobic bacteria, Gram-negative cocci, Gram-positive cocci, and weak action on Gram-positive rods not only endues the composition with antimicrobial activity, but also keeps the function of the composition of the present invention for promoting the growth and acid production of Gram-positive rods. These antibacterial agents and/or bactericides include but are not limited to the following substances: sorbic acid and salts thereof, vitamin $B_1$, vitamin $K_3$, vitamin $K_4$, propanoic acid and salts thereof, acetic acid, dehydro-acetic acid, hydroxybenzoates, hydrogen peroxide, fluconazol, itraconazole, butoconazole, miconazole, clotrimazole, nystatin, metronidazole, lincomycin, amoxicillin, various defensins and antibacterial peptides; wherein the said antibacterial agents and/or bactericides are preferably metronidazole, fluconazole, clotrimazole. The foregoing various antibacterial agents and/or bactericides are selected and used in the present invention according to the knowledge known by those ordinary skilled in the art.

According to the preferable embodiments of the present invention, live lactobacilli can optionally used in manufacture of capsules, microcapsules and tablets comprising simultaneously benzoic acid and/or its sodium salt, saccharide, live lactobacilli, wherein the live lactobacilli is used for directly supplement or replacement of the original lactobacilli in patient's vagina, the saccharide is used for promoting the growth and acid production of the lactobacilli in vagina, and the benzoic acid and/or its sodium salt is used for preventing over-production of acid by the lactobacilli. Thus, the composition comprising benzoic acid and/or its sodium salt, saccharide and live lactobacilli as manufactured according to the present invention is not only very suitable for the treatment of rare lactobacilli in vagina, weaken acidity in vagina, bacterial vaginosis and vaginal dysbacteriosis, but also can be used for treatment of abnormal increase of vaginal acidity, cytolytic vaginosis, lactobacillosis and Candidal vaginitis. The method for preparation and use of the live lactobacilli in the present invention are known by those ordinary skilled in the art.

According to the manufacture use of the present invention, estrogen is also optionally used for manufacturing a composition comprising simultaneously benzoic acid and/or its sodium salt, saccharide, estrogen, wherein the estrogen includes but is not limited to stilbestrol, estradiol, estriol. The estrogen can promote the angiogenesis of vaginal mucosa, epithelial cornification of vaginal mucosa, and epithelial damage healing in vagina, thereby further enhancing therapeutic effects of the composition manufactured according to the present invention. The method for selection and usage of the aforementioned various estrogens in the present invention are known by those skilled in the present art.

The present invention further provides a vaginal composition, which can be a cleaning-nursing agent, a deodorizing agent, a cosmetic, a disinfectant composition or a pharmaceutical composition, characterized in that: (1) comprising benzoic acid and/or its sodium salt, and saccharide as active components; and (2) comprising one or more inactive auxiliary components suitable for human vagina, wherein the saccharide is glucose, fructose, mannose, or oligosaccharides or polysaccharides that can be hydrolyzed to produce glucose, fructose and/or mannose, or any mixture of these saccharides, wherein the said oligosaccharides or polysaccharides include but are not limited to the following: sucrose, maltose, lactose, lactulose, trehalose, cellobiose, melibiose, raffinose, malto-oligosaccharide, isomalto-oligosaccharide, fructo-oligosaccharide, dextrin, starch and glycogen; preferably the said saccharide is glucose, fructose, mannose, sucrose, maltose, trehalose, cellobiose, melibiose, malto-oligosaccharide, fructo-oligosaccharide, dextrin, starch or a mixture thereof; more preferably the said saccharide is glucose, fructose, sucrose, maltose or a mixture thereof.

The vaginal composition according to the present invention can be a cleaning-nursing product, a deodorizing agent, a cosmetic, a disinfectant or a medicine (non-prescription drugs or prescription drugs), the dosage form of which includes but is not limited to water soluble gels, solutions, aerosols, creams, ointments, capsules, microcapsules, suppositories or tablets, preferably water soluble gels, capsules or tablets.

The composition of the present invention is preferably a vaginal water-soluble gel composition, characterized in that: (1) the total amount of benzoic acid and/or its sodium salt, as calculated based on sodium benzoate, is 0.01-5.0% (w/v), preferably 0.1-1.0% (w/v), more preferably 0.2-0.5% (w/v); (2) the total amount of saccharide(s) in the water soluble gel is 0.1-20% (w/v), preferably 0.5-12% (w/v); (3) the inactive auxiliary components are non-flowable, viscous, water-soluble gel matrix, wherein the gel matrix is preferably Xanthan gum, polycarbophil; (4) the composition optionally comprises one or more antibacterial agents and/or bactericides, wherein when the said antibacterial agents and/or bactericides are metronidazole, the concentration of metronidazole is 0.0001-0.1% (w/v), preferably 0.001-0.01% (w/v); (5) the composition further optionally comprises one or more estrogens; (6) the composition is packaged in a sterilizing and sealing manner, preferably a single dose packaged in a sterilizing and sealing manner, and does not contain any live bacterium, fungus or other microorganism.

The present invention further relates to a method for modulating vaginal flora and vaginal acidity, thereby maintaining the pH value of vaginal secretion within the range from 3.5 to 4.5, wherein the method comprises administration of an effective amount of the vaginal composition as prepared according to the present invention in vagina of woman in need thereof. According to the method of the present invention, the method of using the composition comprises administration of the composition in vagina of women in need thereof so that the total daily dosage of benzoic acid and/or its sodium salt, as calculated based on sodium benzoate, is 0.1-750 mg, preferably 1-150 mg, more preferably 2.5-75 mg, the total daily dosage of saccharide is 1-3000 mg, preferably 5-1800 mg, more preferably 50-180 mg, which can be administrated by fractionalizing for 1-3 times per day.

The method of the present invention well solves the problem of how to recovery and maintain normal vaginal flora and vaginal acidity, and can be used for cleaning-nursing vaginal, improving leucorrhoeal property, eliminating or alleviating fishy smell of leucorrhoea, and eliminating or alleviating discomforts such as pruritus vulvae, vulvodynia, etc., and for treatment of lactobacillosis, cytolytic vaginosis, candidal vaginitis, bacterial vaginosis, or vaginal dysbacteriosis.

When therapeutic method of the present invention is used for treatment of the aforementioned vaginal diseases, it may rapidly alleviate the clinical symptoms of patients, recovery and maintain normal vaginal acidity, and therefore is a breakthrough in the field of treatment of vaginal infectious diseases.

SPECIFIC MODELS FOR CARRYING OUT THE INVENTION

Examples of Composition

Example 1

The composition was made by the following method: mixing 0.7 g sodium benzoate, 9.0 g sucrose and 2.5 g Xanthan gum, adding 100 ml distilled water, stirring to dissolve sodium benzoate and sucrose and to swell Xanthan gum to form a homogenous viscous gel; modulating pH value to 6.0; and sterilizing at 112.6° C. for 20 minutes to obtain the water-soluble gel composition of the present invention.

Example 2

By weighing the materials with the following proportion, the composition was made substantially according to the method of Example 1: 9.0 g sucrose, 0.4 g sodium benzoate, 2.5 g Xanthan gum, 100 ml distilled water, pH 7.0, sterilizing, sealing and packaging in form of single dose, 4.0 g per dose.

Example 3

By weighing the materials with the following proportion, the composition was made substantially according to the method of Example 1: 12.0 g sucrose, 0.35 g sodium benzoate, 2.5 g Xanthan gum, 100 ml distilled water, pH 6.5.

Example 4

By weighing the materials with the following proportion, the composition was made substantially according to the method of Example 1: 9.0 g sucrose, 0.5 g sodium benzoate, 3.5 g Xanthan gum, 100 ml distilled water, pH 6.5.

Example 5

By weighing the materials with the following proportion, the composition was made substantially according to the method of Example 1: 6.0 g sucrose, 0.25 g sodium benzoate, 2.5 g Xanthan gum, 100 ml distilled water, pH 6.5.

Example 6

By weighing the materials with the following proportion, the composition was made by: mixing 45.0 g sucrose, 441 g fructo-oligose, 3.5 g sodium benzoate, 10 g oxyphilic lactobacilli powder (containing fructo-oligose and $5 \times 10^{10}$ CFU alive bacteria), sub-packaging in 1000 capsules, wherein each capsule contained 45 mg sucrose, 451 mg fructo-oligose, 3.5 mg sodium benzoate, $4 \times 10^{7}$ CFU oxyphilic lactobacilli.

Example 7

By weighing the materials with the following proportion, the composition was made substantially according to the method of Example 1: 9.0 g sucrose, 0.5 g sodium benzoate, 0.1 g estriol, 3.0 g Xanthan gum, 87.4 g water, pH 5.5.

Example 8

By weighing the materials with the following proportion, the composition was made substantially according to the method of Example 1: 0.1 g fructose, 1.5 g sodium benzoate, 3.0 g Xanthan gum, 100 ml distilled water, pH 5.0.

Example 9

By weighing the materials with the following proportion, the composition was made substantially according to the method of Example 1: 5.0 g mannose, 0.5 g sodium benzoate, 3.5 g Xanthan gum, 100 ml distilled water, pH 6.5.

Example 10

By weighing the materials with the following proportion, the composition was made substantially according to the method of Example 1: 2.0 g glucose, 0.7 g sodium benzoate, 2.5 g Xanthan gum, 94.5 g distilled water, pH 6.5.

Example 11

By weighing the materials with the following proportion, the composition was made substantially according to the method of Example 1: 1.5 g maltose, 0.3 g sodium benzoate, 3.5 g Xanthan gum, 100 ml distilled water, pH 7.2.

Example 12

By weighing the materials with the following proportion, the composition was made substantially according to the method of Example 1: 8.0 g sucrose, 0.5 g sodium benzoate, 3.5 g Xanthan gum, 88 g distilled water, pH 7.2.

Example 13

By weighing the materials with the following proportion, the composition was made substantially according to the method of Example 1: 9.0 g lactose, 0.2 g sodium benzoate, 0.2 g fluconazol, 3.5 g Xanthan gum, 87 g distilled water, pH 6.5.

Example 14

By weighing the materials with the following proportion: 20.0 g starch, 0.2 g sodium benzoate, 0.005 g metronidazole, 1.5 g Xanthan gum, and 100 ml distilled water, the composition was made by firstly mixing starch, sodium benzoate and Xanthan gum, adding 90 ml distilled water, stirring, heating and stirring till boiling, sterilizing; the adding 10 ml sterilized metronidazole solution (containing 0.005 g metronidazole), modulating pH to 7.0 and mixing homogeneously.

Example 15

The materials are weighed in accordance with the following proportion: 5 g glucose, 30 g lactose, 63 g fructo-oligose, 1.0 g sodium benzoate, 0.01 g metronidazole, 0.01 g clotrimazole, 1 g magnesium stearate, then mixed and tableted, wherein each tablet was 0.5 g and comprised 25 mg glucose, 150 mg lactose, 315 mg fructo-oligose, 5 mg sodium benzoate, 0.05 mg metronidazole, 0.05 mg clotrimazole, and 5 mg magnesium stearate.

Example 16

By weighing the materials with the following proportion, the composition was made substantially according to the method of Example 1: 10 g lactose, 0.05 g benzoic acid, 2.0 g polycarbophil, 100 ml distilled water, pH 4.0.

Example 17

By weighing the materials with the following proportion, the composition was made substantially according to the method of Example 1: 0.15 g benzoic acid, 3.0 g glucose, 9.0 g sucrose, 0.15 g fluconazol, 2.5 g Xanthan gum, 100 g distilled water, pH 6.4.

Example 18

The water solution composition was made according to the following proportion and method: weighing 12 g maltose, 0.4 g sodium benzoate, adding 100 ml distilled water, stirring, dissolving, modulating pH to 7.0, sterilizing to obtain the water solution composition.

The beneficial effects of the manufacture use and method of the present invention are illustrated in the following experimental examples.

Experimental Example 1

1. Experimental Object: observing the effects of the compositions of the present invention on pH value of Vaginal secretion and vaginal flora of rhesus monkeys.
2. Experimental Method:
   (1) Preparation of three gels: the following compositions were prepared according to the aforesaid manufacture method by using sodium benzoate, sucrose and Xanthan gum.
       a) The gel as made in Example 1, comprising 0.7 g sodium benzoate, 9.0 g sucrose, 2.5 g Xanthan gum, 100 ml distilled water, modulating pH to 6.0.
       b) 9.0 g sucrose, 2.5 g Xanthan gum, 100 ml distilled water, modulating pH to 6.0.
       c) 0.7 g sodium benzoate, 2.5 g Xanthan, 100 ml distilled water, modulating pH to 6.0.
   The above three gels were sterilized at 112.6° C. for 20 minutes, then standby, wherein a) was the gel of the present invention, while b) and c) were control gels.
   (2) Animals: female rhesus monkeys for the experiments were selected according to the following criterion:
       a) Vaginal secretion pH>4.6;
       b) Nugent score >7 by microscopic examination of Gram-stained vaginal secretion smear;
       12 female rhesus monkeys with body weight of 4-8 kg in compliance with the above criteria were divided into 3 groups, 4 monkeys per group.
   (3) Experimental Steps: 3 groups of rhesus monkeys were separately administrated with the above a), b) and c) gels, 0.5 ml once, 2 times per day, for consecutive 7 days. Vaginal swabs were obtained on the $5^{th}$ day during the administration and on the $3^{rd}$ day after the end of administration. The pH values of vaginal secretions were measured, and the vaginal secretions were smeared, Gram-stained and microscope examined to observe bacterial flora, and marked according to Nugent Score method of vaginal flora. The pH value of Vaginal secretion was measured by using precise pH test paper.

3. Experimental Results: See Tables 1 and 2

(1) Before administration, vaginal secretions of all 12 rhesus monkeys had pH value >4.6, and the Nugent scores of all vaginal flora were >7.

(2) Effects of medicines on pH value of vaginal secretions of rhesus monkeys

Group 1 (gel a): the pH values of vaginal secretions of 4 rhesus monkeys decreased to 3.8, 3.8-4.1 on the $5^{th}$ day of the treatment course, which were obviously lower than the values before administration; on the $3^{rd}$ day after the end of administration, the pH values of vaginal secretions of 3 rhesus monkeys among the 4 rhesus monkeys were lower than 4.6, and the residual one has the pH value of 5.4.

Group 2 (gel b): the pH values of vaginal secretions of 4 rhesus monkeys decreased to below 3.8, 3.8 and 3.8-4.1 on the $5^{th}$ day of treatment course, and the decreasing extent was a little greater than that of Group 1; on the $3^{rd}$ day after the administration, the pH value of Vaginal secretions of all 4 rhesus monkeys were lower than 4.6.

Group 3 (gel c): the pH values of vaginal secretions of 4 rhesus monkeys had no significant change after the administration, and were still 4.8-5.4.

TABLE 1

Effects of different gels on pH values of vaginal secretions of rhesus monkeys with vaginosis

| | Sampling Time | | |
|---|---|---|---|
| Group | Before administration | The $5^{th}$ day of treatment course | The $3^{rd}$ day after the end of administration |
| Group 1 Gel a) | >5.4 | 3.8 | 4.1~4.4 |
| | 5.4 | 3.8 | 4.1~4.4 |
| | >5.4 | 3.8~4.1 | 5.4 |
| | >5.4 | 3.8~4.1 | 3.8 |
| Group 2 Gel b) | >5.4 | 3.8 | 4.1 |
| | 5.4 | 3.8~4.1 | 4.1~4.4 |
| | >5.4 | <3.8* | 3.8* |
| | 5.4 | <3.8 | 4.4 |
| Group 3 Gel c) | 5.4 | 4.8 | 5.4 |
| | 5.4 | 5.4 | 5.4 |
| | >5.4 | 5.4 | >5.4 |
| | 5.4 | 5.4 | >5.4 |

*Fungal spores and hypha were observed under microscopic examination of Gram-stained vaginal secretion smear.

(3) Effects of treatment on Nugent scores of rhesus monkey vaginal flora

Group 1 (gel a): the Nugent scores of vaginal flora of 4 rhesus monkeys decreased to 2-3 on the $5^{th}$ day of the treatment course, which were obviously lower than the scores before the administration; on the $3^{rd}$ day after the end of administration, the scores were still lower than the scores before the administration.

Group 2 (gel b): the Nugent scores of vaginal flora of 4 rhesus monkeys decreased to 2-3 on the $5^{th}$ day of the treatment course, which were obviously lower than the scores before the administration; on the $3^{rd}$ day after the end of administration, the scores were 3-5, still lower than the scores before the administration, wherein fungal spore and hypha were found by both two examinations of vaginal secretions of one rhesus monkey.

Group 3 (gel c): the Nugent scores of vaginal flora of 4 rhesus monkeys had no significant change after the administration, and were still 6-10.

TABLE 2

Effects of different gels on vaginal flora of rhesus monkeys

| | Sampling time | | |
|---|---|---|---|
| Group | Before administration | The $5^{th}$ day of the treatment course | The $3^{rd}$ day after the end of administration |
| Group 1 Gel a) | 8 | 2 | 4 |
| | 7 | 3 | 3 |
| | 8 | 2 | 5 |
| | 9 | 3 | 3 |
| Group 2 Gel b) | 8 | 3 | 3 |
| | 8 | 3 | 4 |
| | 7 | 2** | 3** |
| | 8 | 2 | 5 |
| Group 3 Gel c) | 9 | 10 | 10 |
| | 7 | 8 | 7 |
| | 7 | 9 | 9 |
| | 8 | 6 | 7 |

*Nugent score: 0~3: normal vaginal flora, comprising mainly large Gram-positive rods; >7: bacterial vaginosis flora, comprising mainly Gram-negative or small Gram-variable rods bacteria, Campylobacter, or negative cocci, etc; 4-6: intermediate flora, comprising significantly decreased positive bacilli, and significantly increased negative or small Gram-variable rods bacteria, Campylobacter, etc.
**Fungal spore and hypha were found by staining microscopic examination of vaginal swab specimen smear.

4. Conclusion

The vaginal flora of rhesus monkeys are similar with the vaginal flora of patients with bacterial vaginosis, and contain less large Gram-positive rods but several Gram-negative rods as dominant bacteria. In addition, the pH of vaginal secretion is higher than 4.6, similar to the pH value in vaginal of patients with bacterial vaginosis.

The experimental results indicate that: the gel a) comprising "sodium benzoate+sucrose" as made in Example 1 was able to decrease the Nugent score of rhesus monkey vaginal flora from 7-8 to 2-3, which means the composition "sodium benzoate+sucrose" effectively promoted the growth of vaginal lactobacilli and changed the vaginal flora with dominant Gram-negative rods into the vaginal flora with dominant large Gram-positive rods; the production of acids was enhanced, the vaginal acidity increased, and the pH value of rhesus monkey vaginal secretion, which was 5.4 or above prior to administration, decreased to 3.8, 3.8-4.1.

The gel b) comprising only sucrose was able to decrease rhesus monkey vaginal pH from 5.4 or above to 3.8, 3.8-4.1 and below 3.8; the Nugent score of vaginal flora also decreased from 7-8 to 2-3, wherein fungi were found in vaginal secretion of one rhesus monkey, which implied that the composition comprising only sucrose might cause excessively high vaginal acidity and consequently induced overgrowth of fungi.

In sum, both the composition comprising "sodium benzoate+sucrose" and the composition comprising only sucrose could increase vaginal acidity and promote the growth of vaginal lactobacilli. Their differences lie in that when the gel a) comprising "sodium benzoate+sucrose" was used, the pH of vaginal secretion decreased to 3.8 and the growth of fungi did no occur; but when the gel b) comprising only sucrose was used, the pH value of vaginal secretion decreased to below 3.8 and fungi grew consequently. These results indicate that the composition comprising sodium benzoate and sucrose as active components is more suitable for women in need thereof in comparison with the composition comprising only sucrose as active component. In addition, the composition comprising only sodium benzoate did not exhibit function for promoting the growth of vaginal lactobacilli and decreasing the pH values of rhesus vaginal secretion.

Experimental Example 2

Effects of the Composition of the Present Invention on Women's Vaginal Flora and Acidity 1. Material and Method
(1) Composition: the Gel-A as prepared in Example 2
(2) Patients in group: 12 patients (26-29 years of age) were enrolled according to the following criterion:

a) Leucorrhea was thin and homogenous, gray color, fishy smell, or positive in Whiff test;
b) Pruritus vulvae or vulvodynia;
c) Vaginal secretion smear, Gram-stain, microscopic examination: large Gram-positive rods were less in number, Gram-negative rods or cocci were greater in number, and clue cells >20%;
d) PH value of Vaginal secretion>4.5

2. Treatment and Follow-Up Visit

Gel-A 4.09 was administrated intra-vaginally twice per day for consecutive 5 days. During the treatment course, patients returned to outpatient clinic, participated various tests and were examined by doctor everyday, symptoms and side-effects were recorded, and one administration was conducted. Another administration was conducted by patient at bedtime in home. After the end of treatment course, the patients were follow-up visited for three times.

During the treatment course and the period of follow-up visit, the patients in the group should not wash vagina, should not take any antibacterial agent, and should not have sexual intercourse. If a patient washed vagina or used antibacterial agent, this patient should be excluded from tests. One patient did not complete all test.

3. Results

The results are shown in Table 3. Gel-A exhibited significant effects on women's vaginal flora and vaginal acidity, and was able to maintain them within normal ranges.

TABLE 3

Effects of Gel-A on women's vaginal flora and vaginal acidity

| | Pruritus vulvae | | | Leucorrheal property and smell | | | pH value of Vaginal secretion | | | Clue cells | | | Nugent scores | | |
|---|---|---|---|---|---|---|---|---|---|---|---|---|---|---|---|
| | $V_0$ | $V_3$ | $V_5$ | $V_0$ | $V_3$ | $V_5$ | $V_0$ | $V_3$ | $V_5$ | $V_0$ | $V_3$ | $V_5$ | $V_0$ | $V_3$ | $V_5$ |
| Case 1 | ++ | − | − | + | − | − | 5.4 | 4.1 | 4.1 | + | − | − | 8 | 5 | 3 |
| Case 2 | ++ | − | − | + | − | − | 5.1 | 4.4 | 4.4 | + | − | − | 8 | 3 | 3 |
| Case 3 | ++ | − | − | + | − | − | 5.4 | 4.4 | 4.1 | + | − | − | 9 | 5 | 1 |
| Case 4 | ++ | − | − | + | − | − | 4.6 | 4.4 | 4.1 | + | − | − | 8 | 4 | 4 |
| Case 5 | ++ | ++ | − | + | + | − | 4.6 | 3.8 | 4.1 | + | − | − | 8 | 3 | 1 |
| Case 6 | ++ | + | − | + | + | − | 4.6 | 4.4 | 4.4 | + | − | − | 7 | 2 | 2 |
| Case 7 | ++ | + | − | + | − | − | 4.6 | 4.1 | 4.1 | + | − | − | 7 | 1 | 1 |
| Case 8 | ++ | + | − | + | − | − | 4.6 | 4.1 | 4.1 | + | − | − | 7 | 1 | 1 |
| Case 9 | ++ | − | − | + | − | − | 5.4 | 3.8 | 3.8 | + | − | − | 7 | 0 | 0 |
| Case 10 | ++ | − | − | + | − | − | 5.4 | 4.4 | 4.1 | + | − | − | 9 | 4 | 3 |
| Case 11 | + | − | − | + | − | − | 5.4 | 4.1 | 3.8 | + | − | − | 8 | 5 | 2 |
| Case 12 | + | − | − | + | − | − | 5.1 | 4.1 | 3.8 | + | − | − | 9 | 5 | 0 |

Notation 1: observation time: $V_0$, before the administration of gel; $V_3$, the $3^{rd}$ day of administration of gel; $V_5$, the $5^{th}$ day of administration of gel.
Notation 2: discomforts: ++, obvious pruritus vulvae or vulvodynia; +, slight pruritus vulvae or vulvodynia; −, none of pruritus vulvae or vulvodynia.
Notation 3: leucorrhea property: +, leucorrhea is thin and homogenous, has fishy smell or is positive in Whiff test; −, leucorrhea is thick and viscous, white and turbid or albumen-like, has no fishy smell, and is negative in Whiff test.
Notation 4: Nugent scores (microscopic observation of kinds and amount of bacteria in Gram-stained vaginal secretion smears): 0-3, normal vaginal flora with dominant large Gram-positive rods; 4-6, abnormal flora with decreased amount of large Gram-positive rods and increased amount of cocci and negative rods; 7-9, rare or no large Gram-positive rods, dominant Gram-negative rods and cocci.

(1) After treatment for 3 days, two of 12 women restored all normal indexes: leucorrhea was thick and had no fishy smell, Whiff test was negative, discomforts such as pruritus vulvae and vulvodynia disappeared, the vaginal flora changed and large Gram-positive rods were dominant, clue cells were negative, and pH value of Vaginal secretion was maintained within 3.8-4.4, <4.5.

(2) After treatment for 5 days, 11 of 12 women restored all normal indexes: leucorrheas were thick and had no fishy smell, Whiff tests were negative, discomforts such as pruritus vulvae and vulvodynia disappeared, the vaginal flora changed and large Gram-positive rods were dominant, clue cells were negative, and the pH value of Vaginal secretions were maintained within 3.8-4.4, <4.5.

4. Conclusion

All patients observed in the present example were women with abnormal vaginal flora, weak vaginal acidity, increased the pH value of Vaginal secretion, thin and fishy smell leucorrheas, discomforts such as pruritus vulvae and vulvodynia, and the examination of vaginal flora indicated that Gram-negative rods and cocci were of great amount, while large Gram-positive rods decreased or disappeared. It means that these women actually met the diagnosis criteria of bacterial vaginosis.

Therapeutic results of the present example showed that after intra-vaginal administration of 4.0 g the gel as made in Example 2 twice per day for consecutive 5 days, the bacterial flora with dominant Gram-negative rods or cocci in vagina of most women (11/12) was changed into a flora with dominant large Gram-positive rods, the pH value of women's vaginal secretions decreased from above 4.5 to within 3.5-4.5, and the leucorrhea property of these women was improved, fishy smell disappeared, and discomforts such as pruritus vulvae and vulvodynia were significantly alleviated or eliminated.

Experimental Example 3

A female, 36 years of age, with normal menstruation, no discomforts such as pruritus vulvae and vulvodynia, no fishy smell in leucorrhea, did not have previous genitourinary tract infection history. The pH value of vaginal secretion obtained by vaginal swab was 4.1. By secretion smearing, Gram-staining and microscopic observation, large long Gram-positive rods were found, bacteria of other forms were rare, the epithelial cells of vaginal mucosa were intact, and leukocytes were occasional. It indicated that the woman had normal vaginal flora and vaginal acidity. After administration of 4 g gel as made in Example 3 once per day for consecutive 3 days, the woman did not complain any discomforts or adverse reaction. The pH value of vaginal secretion obtained again by vaginal swab was still 4.1; by secretion smearing, Gram-staining and microscopic observation, the flora was still large Gram-positive rods but with a little short length, bacteria of other forms were still rare, and leukocytes were still occasional. This example showed that the composition of the present invention did not have effect on normal vaginal bacterial flora and normal vaginal acidity.

Experimental Example 4

A female, 29 years of age, had recurrent pruritus vulvae, fishy smell in leucorrhea for one year, more serious after menstruation. She had been treated with several antibacterial agents and lotions, etc, the discomforts were alleviated during administration, but reoccurred after administration. The inventors conducted examination by taking vaginal swab, and found that the pH value of vaginal secretion was 4.8. By secretion smearing, Gram-staining and microscopic observation, the epithelial cells of vaginal mucosa were intact, the vaginal flora was dominant small Gram-variable rods bacteria and Gram-positive cocci, while large Gram-positive rods were rare, and no yeast-like fungal spore was found. She was diagnosed as "bacterial vaginosis", and firstly administrated topically in vagina with 5 g of a composition comprising "9.0 g sucrose, 3.5 g Xanthan, and 100 ml distilled water", twice per day for consecutive 3 days. The patient's leucorrhea amount decreased significantly and fishy smell disappeared, but the patient still felt pruritus vulvae. The pH value of vaginal secretion obtained again by vaginal swab was 3.5. The vaginal flora had dominant large Gram-positive rods, small Gram-variable rods bacteria and Gram-positive cocci were rare. The patient was then administrated topically in vagina with 5 g of the gel as made in Example 4, twice per day for consecutive 2 days. The patient's pruritus vulvae disappeared, the pH value of vaginal secretion obtained again by vaginal swab was 3.8, and the vaginal flora still had dominant large Gram-positive rods. The present example indicated that a composition comprising only sucrose as active component could promote the growth of Gram-positive rods and reduce the pH value of vaginal secretion to 3.5; while the composition comprising sodium benzoate and sucrose as components according to the present invention could also promote the growth of large Gram-positive rods in vagina, reduce the pH value of Vaginal secretion to 3.8, and eliminate fishy smell of woman's leucorrhea and pruritus vulvae, i.e., it can be used not only for treatment of weak vaginal acidity, decreased vaginal Gram-positive rods and bacterial vaginosis, but also does not cause adverse reaction such as over-strong vaginal acidity.

Experimental Example 5

A female, 39 years of age, had recurrent pruritus vulvae, unpleasant odor in leucorrhea, and algopareunia for 3 months. The inventors conducted examination by taking vaginal swab, and found that the pH value of vaginal secretion was 5.4. By smearing secretion, Gram-staining and microscopic observation, a large amount of Gram-negative rods, cocci and positive cocci was found, no large Gram-positive rods was found, and leukocyte was rare. Thus, the patient was diagnosed as "vaginal dysbacteriosis" and "bacterial vaginosis". The patient was administrated topically in vagina with 4 g of the gel as made in Example 5, twice per day for consecutive 5 days. The patient's pruritus vulvae and abnormal odor in leucorrhea disappeared, the pH value of vaginal secretion obtained again by vaginal swab was 3.5, and the vaginal flora had dominant large Gram-positive rods, and rare other bacteria. The present example indicated that the composition of the present invention could eliminate woman's pruritus vulvae and abnormal odor in leucorrhea, promote the growth of vaginal Gram-positive rods, increase vaginal acidity, and exhibit therapeutic effects on vaginal dysbacteriosis and bacterial vaginosis.

Experimental Example 6

A female, 41 years of age, had recurrent pruritus vulvae, algopareunia, and increased leucorrhea with unpleasant odor for more than half of year. The inventors conducted examination by taking vaginal swab, and found that the pH value of vaginal secretion was 5.4. By smearing secretion, Gram-staining and microscopic observation, the epithelial cells of vaginal mucosa had intact structure, leukocytes were occasional, the vaginal flora had a large amount of small Gram-negative rods, large Gram-positive rods were rare. Thus, the patient was diagnosed as "bacterial vaginosis". The patient was administrated topically in vagina with one capsule as made in Example 6, once per day for consecutive 5 days. The woman's leucorrhea decreased significantly, abnormal odor in leucorrhea disappeared, pruritus vulvae and algopareunia disappeared, the pH value of vaginal secretion obtained again by vaginal swab was 4.1, the vaginal flora had dominant large Gram-positive rods, and small Gram-negative rods decreased significantly. The present example indicated that the composition comprising sodium benzoate, sucrose, fructo-oligosaccharide and lactobacilli as active components according to the present invention could modulate vaginal flora and vaginal acidity, eliminate woman's pruritus vulvae, algopareunia and abnormal odor in leucorrhea, and could be used for treatment of weak vaginal acidity and bacterial vaginosis.

Experimental Example 7

A female patient, 54 years of age, had increased leucorrhea and pruritus vulvae for two years, wherein leucorrhea usually was in water-like form, occasionally was in yellow-green color, and the patient sometimes had frequent micturition and odynuria. The inventors conducted examination by taking vaginal swab, and found that the pH value of vaginal secretion was higher than 5.4. By smearing secretion, Gram-staining and microscopic observation, a relative large amount of low layer mucosa epithelial cells were found, bacteria were relative less, a small amount of Gram-positive cocci were found, and no fungal spore, Trichomonas, etc was found. Thus, the patient was diagnosed as "weak vaginal acidity", "decreased vaginal lactobacilli" and "senile vaginitis". The patient was administrated topically in vagina with 5 g of the gel as made in Example 7, once per day for consecutive 7 days. The patient's leucorrhea decreased significantly, the pruritus vulvae and vulvodynia were significantly alleviated, the pH value of vaginal secretion obtained again by vaginal swab was 4.1, the vaginal flora had dominant large Gram-positive rods, the low layer cells in vaginal mucosa epithelial cells decreased while surface layer cells increased. The present example indicated that the composition comprising sodium benzoate, sucrose and estriol as active components according to the manufacture use and therapeutic method of the present invention could eliminate or alleviate woman's pruritus vulvae and vulvodynia, improve leucorrhea property, increase vaginal acidity, restore vaginal lactobacilli, and effectively control the symptoms and conditions of patients with senile vaginitis.

Experimental Example 8

A female, 35 years of age, had pruritus vulvae and vulvodynia for 5 months, serious before menstruation. The pH value of vaginal secretion was lower than 3.5. By smearing secretion, Gram-staining and microscopic observation, large Gram-positive rods were found, no yeast-like fungal spore and hypha were found, the vaginal mucosa epithelial cells were not intact in shape and structure and contained broken cells, and naked nucleus were found. Thus, the patient was diagnosed as "over-strong vaginal acidity" and "Cytolytic vaginosis". The patient was administrated topically in vagina with 4 g of the gel as made in Example 8, twice per day for consecutive 5 days. The woman's pruritus vulvae and vulvodynia disappeared, the pH value of vaginal secretion obtained again by vaginal swab was 4.4, the vaginal flora had dominant large Gram-positive rods, the vaginal mucosa epithelial cells had intact shape, and no broken cell and naked nucleus were found.

Experimental Example 9

A female, 35 years of age, had recurrent pruritus vulvae, vulvodynia and increased leucorrhea for about one year, diagnosed as vaginitis for several times in hospitals. The symptoms were alleviated by treatment with antifungal agent such as Daktarin, etc., but reoccurred after drug withdrawal. The inventors conducted examination, and found that the pH value of vaginal secretion was 3.5. By smearing secretion, Gram-staining and microscopic observation, the vaginal flora had large Gram-positive rods with long body, no yeast-like fungal spore and hypha were found, the broken epithelial cells were occasional. Thus, the patient was diagnosed as "over-strong vaginal acidity" and "lactobacillosis". The patient was administrated topically in vagina with 3 g of the gel as made in Example 9, once per day for consecutive 5 days. The woman's pruritus vulvae and vulvodynia disappeared, leucorrhea decreased significantly, the pH value of vaginal secretion obtained again by vaginal swab was 4.1, the vaginal flora still had dominant large Gram-positive rods but with short body, no yeast-like fungal spore was found. The results indicated that the composition comprising sodium benzoate and mannose as active component according to the present invention could eliminate women's pruritus vulvae and vulvodynia, modulate normal vaginal acidity, and exhibit therapeutic effects on over-strong vaginal acidity and lactobacillosis.

Experimental Example 10

A female patient, 31 years of age, had pruritus vulvae and increased leucorrhea for one year, was diagnosed as "Candidal vaginitis" for several times, and treated with antifungal agents such as nystatin effervescent tablets and Daktarin suppositories, etc., but although the symptoms were alleviated during administration, they reoccurred after administration usually. The inventors conducted examination and found that the pH value of vaginal secretion was 3.8. By smearing secretion, Gram-staining and microscopic observation, the vaginal flora was large long Gram-positive rods, no bacteria with other forms were found, and no yeast-like fungi were found. Thus, the patient was diagnosed as "lactobacillosis". The patient was administrated topically in vagina with 5 g of the gel as made in Example 10, twice per day for consecutive 3 days. The leucorrhea decreased, the vaginal discomforts disappeared, the pH value of vaginal secretion obtained again by vaginal swab was 3.8-4.1, the vaginal flora still was large Gram-positive rods but became shorter significantly, and no broken epithelial cell and naked nucleus were found. The results showed that the composition comprising sodium benzoate and glucose as active components according to the present invention could eliminate woman's pruritus vulvae and increased leucorrhea, and could be used for treatment of vaginal lactobacilli overgrowth and lactobacillosis.

Experimental Example 11

A female, 33 years of age, had recurrent pruritus vulvae and increased leucorrhea for 3 months, and was treated with antifungal agents, but therapeutic effects were not good. The pH value of vaginal secretion was 3.0. By smearing secretion, Gram-staining and microscopic observation, broken vaginal mucosa epithelial cells with incomplete shape and structure were found, naked nucleus of epithelial cells were found; the vaginal flora was large Gram-positive rods, and no yeast-like fungal spore were found. Thus, the patient was diagnosed as "over-strong vaginal acidity" and "Cytolytic vaginosis". The patient was administrated topically in vagina with 5 g of the gel as made in Example 11, three times per day for consecutive 3 days. The woman's pruritus vulvae disappeared, the leucorrhea decreased significantly, the pH value of vaginal secretion obtained again by vaginal swab was 3.8, the vaginal flora still was large Gram-positive rods, the mucosa epithelial cells were intact, and no broken epithelial cell and naked nucleus were found. The results showed that the composition comprising sodium benzoate and maltose as active components according to the present invention could modulate and maintain normal vaginal acidity, eliminate woman's discomforts such as pruritus vulvae, and could be used for treatment of over-strong vaginal acidity and Cytolytic vaginosis.

Experimental Example 12

A female, 40 years of age, had recurrent vulvodynia and increased leucorrhea for one year, and was treated with antifungal agents, and the symptoms were alleviated during administration. The inventors conducted examination by taking vaginal swab and found that the pH value of vaginal secretion was below 3.8. By smearing secretion, Gram-staining and microscopic observation, a relative large amount of fragments of broken vaginal mucosa epithelial cells and naked nucleus of epithelial cells were found; the vaginal flora was large
Gram-positive rods, and no yeast-like fungal spore were found. Thus, the patient was diagnosed as "over-strong vaginal acidity" and "Cytolytic vaginosis". The patient was administrated topically in vagina with 3 g of the gel as made in Example 12, twice per day for consecutive 3 days. The patient's vulvodynia disappeared, the leucorrhea decreased, the pH value of vaginal secretion obtained again by vaginal swab was 4.1, and the vaginal flora still was large Gram-positive rods. After the patient was further treated for 2 days, the pH value of vaginal secretion was still 4.1, the vaginal flora was still large Gram-positive rods, and no broken epithelial cell and naked nucleus were found. The results showed that the composition comprising benzoic acid and sucrose as active components according to the present invention could eliminate woman's vulvodynia, improve leucorrhea property, modulate vaginal acidity, and could be used for treatment of over-strong vaginal acidity and Cytolytic vaginosis.

Experimental Example 13

A female, 28 years of age, had pruritus vulvae and increased leucorrhea for 2 months. The pH value of vaginal secretion was 4.1. By smearing secretion, Gram-staining and microscopic observation, no cytolyzed and broken vaginal mucosa epithelial cells and naked nucleus were found; the vaginal flora was dominant large Gram-positive rods, Gram-positive cocci and Gram-negative rods. Yeast-like fungal spore and hypha were found. Thus, the patient was diagnosed as "Candidal vaginitis". The patient was administrated topically in vagina with 4 g of the gel as made in Example 13, twice per day for consecutive 5 days. The patient's leucorrhea decreased significantly, symptoms such as pruritus vulvae disappeared, the pH value of vaginal secretion obtained again by vaginal swab was 4.1, the vaginal flora still was dominant large Gram-positive rods, the Gram-positive cocci and small Gram-negative rods decreased significantly, and no yeast-like fungal spore and hypha were found. The results showed that the composition comprising sodium benzoate, lactose and fluconazol as active components according to the present invention could treat "Candidal vaginitis", modulate vaginal flora, maintain dominant Gram-positive rods, and reduce Gram-positive cocci and negative rods.

Experimental Example 14

A female, 35 years of age, had pruritus vulvae, increased leucorrhea with fishy smell for two years. The inventors conducted examination by taking vaginal swab and found that the pH value of vaginal secretion was below 5.4. By smearing secretion, Gram-staining and microscopic observation, the vaginal mucosa epithelial cells were intact in shape and structure, a large amount of Gram-positive cocci and small Gram-negative rods were found, while large Gram-positive rods are rare. Thus, the patient was diagnosed as "vaginal dysbacteriosis" and "bacterial vaginosis". The patient was administrated topically in vagina with 4 g of the gel as made in Example 14, twice per day for consecutive 3 days. The patient's leucorrhea decreased significantly, the fishy smell disappeared, the pruritus vulvae disappeared, the pH value of vaginal secretion obtained again by vaginal swab was 4.1, the vaginal flora was dominant large Gram-positive rods, and Gram-positive cocci and small Gram-negative rods were rare. The results showed that the composition comprising sodium benzoate, metronidazole and starch as active components according to the present invention could promote the growth of large Gram-positive rods, increase vaginal acidity, eliminate woman's leucorrhea fishy smell and pruritus vulvae, and could be used for treatment of weak vaginal acidity, vaginal dysbacteriosis and bacterial vaginosis.

Experimental Example 15

A female, 27 years of age, had pruritus vulvae and leucorrhea with fishy smell for two months. The pH value of vaginal secretion was 4.8. By smearing secretion obtained from vaginal swab, Gram-staining and microscopic observation, a large amount of Gram-negative rods and cocci with various shapes, as well as Gram-positive cocci with various shapes were found, yeast-like bacteria were found, no large Gram-positive rods were found, and a small amount of leukocytes were found. Thus, the patient was diagnosed as "bacterial vaginosis" in combination with "Candidal vaginitis". The patient was administrated with one tablet as made in Example 15, twice per day for consecutive 5 days. The patient's pruritus vulvae disappeared, the leucorrhea had no fishy smell, the pH value of vaginal secretion obtained again by vaginal swab was 4.4. By smearing vaginal secretion, Gram-staining and microscopic observation, the vaginal flora was dominant large Gram-positive rods, and bacteria with other forms were rare, no yeast-like bacteria were found, and leukocytes decreased.

Experimental Example 16

A female, 33 years of age, had recurrent fishy smell of leucorrhea in combination with algopareunia for 5 months. The pH value of vaginal secretion was 5.4. By smearing secretion, Gram-staining and microscopic observation, the vaginal flora was dominant Gram-variable Mobilunci. Thus, the patient was diagnosed as "bacterial vaginosis". The patient was administrated with the gel as made in Example 16, once per day for consecutive 3 days. The fishy smell of leucorrhea disappeared, and the pH value of vaginal secretion obtained again by vaginal swab was 4.0. By smearing secretion, Gram-staining and microscopic observation, the vaginal flora was dominant large Gram-positive rods, and bacteria with other forms were rare.

Experimental Example 17

A female, 35 years of age, had recurrent pruritus vulvae and vulvodynia for half of year. The pH value of vaginal secretion was 3.5. By smearing secretion, Gram-staining and microscopic observation, the vaginal flora was dominant large Gram-positive rods, fungal spore and hypha, fragments of epithelial cells and naked nucleus were found, and a large number of leukocytes was found. Thus, the patient was diagnosed as "Candidal vaginitis" in combination with "Cytolytic vaginosis". The patient was administrated with the gel as made in Example 17, twice per day for consecutive 5 days. The symptoms disappeared. The pH value of vaginal secretion was 4.1. By smearing secretion, no fungal spore and hypha were found, no epithelial cell fragment and naked nucleus were found, and leukocytes decreased significantly.

Experimental Example 18

A female, 44 years of age, had recurrent pruritus vulvae in combination with increased leucorrhea for two years. The pH value of vaginal secretion was 5.4. By smearing vaginal secretion, Gram-staining and microscopic observation, the vaginal flora was dominant small Gram-variable rods. Thus, the patient was diagnosed as "bacterial vaginosis". The cotton balls saturated with the solution as made Example 18 were placed into the woman's vagina, once per day for consecutive 3 days. The leucorrhea decreased significantly, pruritus vulvae disappeared, and the pH value of vaginal secretion was 4.1. By smearing vaginal secretion, Gram-staining and microscopic observation, the vaginal flora was dominant large Gram-positive rods, and bacteria with other forms were rare.

The invention claimed is:

1. A method for two-phase modulating vaginal flora and vaginal acidity thereby maintaining the pH value of vaginal secretion within a range from 3.5 to 4.5, said method is conducted by promoting Gram-positive bacilli to multiply and produce acids in vagina when the Gram-positive bacilli in vagina are rare and the vaginal acidity is over 4.6, and inhibiting the production of acids in the vagina when the Gram-positive bacilli in vagina are abundant and the vaginal acidity is below 4.0;
wherein said method comprises administrating an effective amount of a vaginal composition, said vaginal composition consists of the following components:
(1) benzoic acid and/or its sodium salt, together with saccharide(s) as the sole active ingredients; wherein the total amount of benzoic acid and/or its sodium salt, calculated based on sodium benzoate, is 0.1-1.0% (w/v), the total amount of saccharide in the composition is 0.1-20% (w/v);
(2) one or more inactive excipient(s) suitable for human vagina; wherein said inactive excipient is a non-flowable, viscous, water-soluble gel matrix, and it is selected from Xanthan gum and polycarbophil;
wherein said saccharide is glucose, fructose, mannose, or oligosaccharides or polysaccharides that can be hydrolyzed in vivo or in vitro to produce glucose, fructose and/or mannose, or any mixture of these saccharides, wherein said oligosaccharides or polysaccharides are selected from the group consisting of the following: sucrose, maltose, lactulose, trehalose, cellobiose, melibiose, raffinose, malto-oligosaccharide, isomalto-oligosaccharide, fructo-oligosaccharide, dextrin, starch and glycogen;
wherein said vaginal composition is a cleaning-nursing product, a deodorizing agent, a cosmetic, an antimicrobial composition or a pharmaceutical composition, said composition is a non-flowable, viscous, water-soluble gel, said composition does not comprise live bacteria, fungi or other microorganisms; the pH value of the composition is within the range from 4.5 to 7.5.

2. The method according to claim 1, it is for cleaning-nursing vagina, eliminating or alleviating unpleasant odor of vaginal secretion, and eliminating or alleviating discomforts such as pruritus vulvae, vulvodynia, algopareunia, etc.

3. The method according to claim 1, it is for treating Lactobacillosis, Cytolytic vaginosis, Candidal vaginitis, Bacterial vaginosis, or vaginal dysbacteriosis.

4. The method according to claim 1, wherein the vaginal composition is selected from the group consisting of the following vaginal dosage forms:
water-soluble gels, creams, or ointments.

5. A method for two-phase modulating vaginal flora and vaginal acidity thereby maintaining the pH value of vaginal secretion within a range from 3.5 to 4.5, said method is conducted by promoting Gram-positive bacilli to multiply and produce acids in vagina when the Gram-positive bacilli in vagina are rare and the vaginal acidity is over 4.6, and inhibiting the production of acids in the vagina when the Gram-positive bacilli in vagina are abundant and the vaginal acidity is below 4.0; wherein said method comprises administrating an effective amount of a vaginal composition, said vaginal composition consists of the following components:
(1) benzoic acid and/or its sodium salt, together with saccharide(s) as the sole active ingredients; wherein the total amount of benzoic acid and/or its sodium salt, calculated based on sodium benzoate, is 0.1-1.0% (w/v), the total amount of saccharide in the composition is 0.1-20% (w/v);
(2) estrogen, which is selected from the group consisting of stilbestrol, estradiol and/or estriol;
(3) one or more inactive excipient(s) suitable for human vagina; wherein said inactive excipient is a non-flowable, viscous, water-soluble gel matrix, and it is selected from xanthan gum and polycarbophil;
wherein said saccharide is glucose, fructose, mannose, or oligosaccharides or polysaccharides that can be hydrolyzed in vivo or in vitro to produce glucose, fructose and/or mannose, or any mixture of these saccharides, wherein said oligosaccharides or polysaccharides are selected from the group consisting of the following: sucrose, maltose, lactulose, trehalose, cellobiose, melibiose, raffinose, malto-oligosaccharide, isomalto-oligosaccharide, fructo-oligosaccharide, dextrin, starch and glycogen;
wherein said vaginal composition is a cleaning-nursing product, a deodorizing agent, a cosmetic, an antimicrobial composition or a pharmaceutical composition,
said composition is a non-flowable, viscous, water-soluble gel,
said composition does not comprise live bacteria, fungi or other microorganisms; and
the pH value of the composition is within the range from 4.5 to 7.5.

6. The method according to claim 1, wherein the said composition further optionally comprises live lactobacilli and/or other live lactic-acid-producing bacteria.

7. The method according to claim 1, wherein in said composition, the total amount of benzoic acid and/or its sodium salt, calculated based on sodium benzoate, is 0.2-0.5% (w/v); the total amount of said saccharide(s) in the water-soluble gel composition is 0.5-12%(w/v).

8. The method according to claim 1, wherein in said composition, said saccharide is glucose, fructose, mannose, sucrose, maltose, trehalose, cellobiose, melibiose, malto-oligosaccharide, fructo-oligosaccharide, dextrin, starch, or a mixture thereof.

9. The method according to claim 8, wherein in said composition, said saccharide is glucose, fructose, sucrose, maltose, trehalose, or a mixture thereof.

10. The method according to claim 1, wherein said composition is a single dose packaged in a sterilizing and sealing manner.

11. The method according to claim 4, wherein the vaginal composition is selected from the group consisting of water-soluble gels.

12. The method according to claim 4, wherein the vaginal composition is a vaginal dosage form of water soluble gels.

\* \* \* \* \*